United States Patent [19]
Desai et al.

[11] Patent Number: 5,945,519
[45] Date of Patent: Aug. 31, 1999

[54] PROCESS FOR THE PREPARATION OF SUCROSE FATTY ACID ESTERS

[75] Inventors: Natvarlal Desai, Dinslaken; Burghard Grüning, Essen, both of Germany

[73] Assignee: Th Goldschmidt AG, Essen, Germany

[21] Appl. No.: 09/088,881

[22] Filed: Jun. 2, 1998

[30] Foreign Application Priority Data

Jun. 17, 1997 [DE] Germany .............................. 197 25 548

[51] Int. Cl.$^6$ .............................. C07H 1/00; C07H 15/00; C07H 15/06
[52] U.S. Cl. ........................ 536/18.6; 536/18.5; 536/115; 536/116; 536/119; 536/120; 536/124
[58] Field of Search ................................... 536/115, 116, 536/119, 120, 124, 18.5, 18.6

[56] References Cited

U.S. PATENT DOCUMENTS 4,840,815  6/1989  Meyer et al. .............................. 426/611
5,681,948  10/1997  Miller et al. .............................. 536/115

*Primary Examiner*—Elli Peselev
*Attorney, Agent, or Firm*—Scully, Scott, Murphy & Presser

[57] ABSTRACT

The invention relates to a process for the solvent-free preparation of sucrose fatty acid esters, their mixtures with nonsugar polyol fatty acid esters, and in particular of sucrose glycerides. In a first process step, sucrose is reacted with fatty acid alkyl esters in the presence of basic catalyst at reduce pressure and elevated temperature. In a further reaction step, the reaction mixture obtained above is reacted at reduced pressure and elevated temperature with 0.1 to 0.5 mol of polyol per mole of fatty acid alkyl ester employed and then filtered. The products of the process according to the invention have very high sucrose ester contents. They are free of undesired, unreacted alkyl ester.

13 Claims, No Drawings

PROCESS FOR THE PREPARATION OF SUCROSE FATTY ACID ESTERS

FIELD OF THE INVENTION

The invention relates to a process for the solvent-free preparation of sucrose fatty acid esters, their mixtures with nonsugar polyol fatty acid esters and in particular of sucrose glycerides.

BACKGROUND OF THE INVENTION

Sucrose fatty acid esters have been the subject of intensive investigations for decades, since they can be prepared from renewable, inexhaustible natural substances, such as sugars and fats. Both substance groups are employed as valuable, mild, physiologically acceptable and biodegradable additives in cosmetics, pharmacy, in foodstuffs, in animal feeds and as agrochemicals, for example for keeping fruit fresh.

Sucrose glycerides represent a particular form of the supply of sucrose fatty acid esters. In general, they are mixtures of sucrose esters and glycerides. According to European Standard E474, sucrose glycerides which are permitted for the foodstuffs sector must contain at least 40% of sucrose esters and at least 40% of glycerides.

The prior art discloses a number of processes for the preparation of sucrose esters. Thus the reaction of fatty acid methyl esters with sucrose in the presence of basic catalysts in various solvents, such as dimethylformamide or dimethyl sulfoxide as a solvent, is described, see, for example DE-C-10 52 388 or DE-C-12 62 988.

A great disadvantage of this process is that the solvents dimethylformamide (DMF) or dimethyl sulfoxide (DMSO) have to be removed from the reaction mixture without residue after the transesterification, in particular if the products are to be employed in the foodstuffs sector.

In principle, sucrose glycerides can be prepared by means of the transesterification of natural fats or vegetable oils with sucrose. An economical preparation of sucrose glycerides by means of transesterification on an industrial scale, however, is hardly realizable, since the resulting glycerol can only be removed with difficulty because of its high boiling point. Moreover, the thermal instability and the relatively limited solubility of sucrose in organic solvents causes considerable problems. The solvents, for example DMF, DMSO, N-methylpyrrolidone (MNP) or pyridine, must therefore be added in a large excess and yet removed without residue after the reaction. Thus DE-C-11 93 026 describes a process for the preparation of poly fatty acid esters of nonreducing oligosaccharides by transesterifying a nonreducing oligosaccharide with fatty acid esters of nonsugar alcohols, the reaction being carried out in the presence of a transesterification catalyst in the presence of pyridine as a reaction medium.

Similarly, U.S. Pat. No. 3,349,081 describes a process for the preparation of sucrose esters by transesterification of sucrose with natural triglycerides in dimethylformamide, followed by stripping off the reaction solvent and treating the residue with an aqueous/butanolic sodium chloride solution and evaporating the separated butanol layer to dryness.

Furthermore, the preparation of sucrose glycerides from tallow or palm kernel oil and sucrose in dimethylformamide is known from L. Bobichon, ACS Syn. Ser (1977), 41, Sucrochemistry Sympo. 1976, pp. 115 to 120. The products, CELINOLS®, contain 39 to 42% of sucrose esters, 50 to 55% of glycerides and 50 to 100 ppm of DMF and are recommended as animal feed additives.

Recently, attempts have been made to avoid the disadvantages of the prior art caused by the use of solvents. GB-A-1 399 053 discloses a solvent-free transesterification process for the preparation of sucrose esters. According to this process, the transesterification of fatty acid glycerides with sucrose is carried out at 110 to 140° C., in particular under the action of potassium carbonate in an amount from 5 to 12%, based on the total weight of the reaction mixture. The products obtained by this process are very dark, in particular brown, waxy materials. Moreover, the total yield of mono- and disucrose esters is clearly below 30%. This process yields a complex reaction mixture which to a high extent contains nonreacted starting materials.

GB-A-1 499 989 likewise describes the reaction of solid sucrose with an alkyl ester of a fatty acid having 1 to 6 carbon atoms in the alcohol unit and at least 8 carbon atoms in the fatty acid unit, the reaction being carried out in the presence of basic transesterification catalysts at a temperature of 110 to 140° C. under atmospheric pressure in the absence of solvents. Here too, as can be seen from the working examples, potassium carbonate is particularly preferably employed as a catalyst. Despite the high amount of basic catalyst used and very long reaction time of 6 to 23 hours, the two abovementioned processes give very low yields of sucrose esters. Moreover, the reaction mixtures contain, to a considerable extent, unreacted alkyl esters, glycerides, soaps and sucrose. According to the product composition described therein, reaction mixtures of this type can hardly be suitable for foodstuff uses or even fulfill the requirements of the EC standard E474 for foodstuff emulsifiers.

FR-A-2 463 152 discloses a further process for the preparation of sucrose glycerides, in which in the first reaction stage a limited alcoholysis of the triglyceride with alcohol takes place at 80 to 180° C. with addition of the basic catalyst potassium carbonate. In the second reaction stage, the mixture of alkyl ester, triglyceride and soap is transesterified with sucrose with fresh addition of potassium carbonate. The process thus comprises two reaction steps, necessitates the use of high amounts of catalyst and soaps and at the same time, however, yields a reaction mixture of sucrose esters (40 to 49%), glycerides and high amounts of undesired, unreacted alkyl esters (2 to 20%) as well as soap and sucrose.

EP-A-0 404 226 discloses a process for the purification of product-containing esters of nonreducing sugars and one or more fatty acids. In this case, the crude esterification product is subjected to an extraction with supercritical carbon dioxide in a complicated process.

DE-A-41 31 505 relates to a process for the work-up of the reaction mixture obtained in the solvent-free preparation of sucrose fatty acid esters by transesterification of sucrose with fatty acid alkyl esters, in particular fatty acid methyl esters, in the presence of a basic transesterification catalyst. In order to improve the economy of the process with identical or even improved quality of the final product, it is proposed that unreacted sucrose is filtered off at a temperature between the melting points of the sucrose employed and of the sucrose ester prepared and then unreacted alkyl esters are distilled off from the reaction mixture.

BRIEF SUMMARY OF THE INVENTION

The object of the present invention is to make available a process for the solvent-free preparation of sucrose fatty acid esters—also abbreviated to sucrose esters—and their mixtures with nonsugar polyol fatty acid esters, in particular of sucrose glycerides, which can be carried out in a simple manner, is particularly suitable for use on an industrial scale and at the same time avoids the problems of the prior art arising due to use of toxic solvents and due to complicated and costly purification steps.

The process should expediently afford sucrose esters in high yields, from which sucrose glycerides conforming to EC standard E474 can optionally be produced by simple admixture of glycerides.

The abovementioned object is achieved according to the invention in a first embodiment by a process for the solvent-free preparation of sucrose fatty acid esters, in which a) sucrose is reacted with one or more fatty acid alkyl esters of a chain length of 6 to 20 carbon atoms in the straight-chain or branched, saturated, mono- or polyunsaturated fatty acid radical and 1 to 6 carbon atoms in the straight-chain or branched alcohol radical, in the presence of basic catalyst at reduced pressure and elevated temperature, wherein b) the reaction mixture according to a) is reacted at reduced pressure and elevated temperature with 0.01 to 0.5 mol of polyol per mole of fatty acid alkyl ester employed and then c) filtered without addition of solvent.

The advantage of the process according to the invention in particular consists in avoiding, in a very simple manner, the disadvantages of the prior art as a result of carrying out the reaction in toxic solvents and of the complicated and costly extraction in organic solvents or in supercritical solvents such as carbon dioxide, and the molecular distillation of the unreacted alkyl esters. The process according to the invention therefore offers a high economy.

The sucrose fatty acid esters of the process according to the invention have very high sucrose ester contents and are furthermore free of undesired, unreacted alkyl esters. The content of unreacted sucrose in the products according to the invention is very low.

It is readily possible with the aid of the invention to prepare glycerides which contain more than 80% by weight of sucrose esters and thus also fulfill the specification of the EC standard D473 (sucrose esters) and are therefore additionally useful and of interest for the foodstuffs sector.

DETAILED DESCRIPTION OF THE INVENTION

Possible fatty acid esters for carrying out the process according to the invention are both straight-chain or branched, saturated, mono- or polyunsaturated fatty acid alkyl esters having a chain length of 6 to 20 carbon atoms in the fatty acid radical. Particularly preferred in the sense of the present invention are fatty acid alkyl esters having a chain length of 12 to 18 carbon atoms in the fatty acid radical. The choice of the alcohol groups of the fatty acid alkyl esters is unrestricted in principle. Particularly preferably in the sense of the present invention, however, the methyl ester is employed. Instead of the pure fatty acid alkyl esters having a defined chain length of the fatty acid radical, it is of course also possible to employ customary fatty acid alkyl ester mixtures.

Suitable polyols are those nonsugar alcohols which have more than one hydroxyl group. Suitable polyols are, for example, 1,2-propylene glycol, glycerol, sorbitol and also condensation products of glycerol, such as di-, tri- or tetra-glycerol or mixtures thereof. A particularly preferred polyol is glycerol. If glycerol is employed, sucrose glycerides result.

The alkaline catalysts suitable for the process of the invention include various inorganic salts, such as oxides, carbonates, hydroxides, hydrogencarbonates, and also potassium, sodium, magnesium, zinc and lithium soaps of the fatty acids having a chain length of 8 to 20 carbon atoms in the straight-chain or branched, saturated, mono- or poly-unsaturated fatty acid radicals. The inorganic salts can be used on their own or alternatively in combination with the soaps mentioned. In the sense of the present invention, the presence of 0.5 to 5% by weight of the catalyst, based on the weight of the reaction mixture, is particularly preferred.

To carry out the process according to the invention, the individual components are weighed in. The transesterification is preferably carried out at a temperature in the range from 120 to 160° C., in particular at 120 to 145° C. in vacuo, that is to say at reduced pressure, which is preferably 25 to 100 mbar, in particular in the course of 2 to 6 hours. In this case, an equimolar ratio of fatty acid alkyl ester to sucrose can be set. Moreover, it is, however, preferred to employ an excess of fatty acid alkyl ester, in particular fatty acid methyl ester, to sucrose. Particularly preferably in the sense of the present invention, this range is set in the ratio from 1 to 3.5 mol of fatty acid alkyl ester to 1 mol of sucrose.

Following the esterification of the sucrose, the reaction mass is optionally cooled, and is then reacted at reduced pressure and elevated temperature with 0.01 and 0.5 mol of polyol per mole of fatty acid alkyl ester employed. It is particularly preferred in the present invention to carry out this reaction at 90 to 130° C., and at a pressure of 25 to 100 mbar in the course of 0.5 to 3 hours.

Surprisingly, it has been found that, in the process according to the invention, unreacted fatty acid alkyl esters are preferentially transesterified to polyol esters, in particular to glycerides, and in this case no noticeable transesterification of the sucrose ester takes place.

The reaction products obtained according to the invention can, if required, be neutralized by processes known per se, which are disclosed, for example, in DE-A-41 31 505, using inorganic acids and/or bleached using hydrogen peroxide at elevated temperature, for example at 80° C., in the course of 30 min. Particularly preferably in the sense of the present invention, the sucrose esters are filtered as a mixture with fatty acid polyol ester, in particular sucrose glyceride, as a crude reaction product at 80 to 100° C., optionally with addition of filter aid, and 0.5 to 2 bar without addition of organic or inorganic solvents.

If desired, the viscous reaction products are mixed with water at 60 to 70° C. in order to obtain them in pasty form or, depending on use requirements, mixed with glycerides, other active compounds and/or emulsifiers and pelleted. The products obtainable by the process according to the invention are pale to cream-colored, odorless and can be employed without further purification in cosmetics, pharmacy or, if glycerol is used as the polyol, in foodstuffs.

The following working examples illustrate the invention in greater detail.

EXAMPLE 1

In a three-necked flask with a vacuum-tight stirrer, controllable temperature-measuring device and descending condenser with a coolable receiver, 207 g (0.965 mol) of methyl laurate was transesterified at 135° C. and 100 mbar vacuum in the course of 5 hours using 102 g (0.299 mol) of sucrose, 3 g of potassium carbonate and 3 g of sodium stearate. A dark-brown viscous mass of composition A was formed (see Table 1 which follows). The reaction mass was cooled to 90°

C. and then reacted with 5 g of glycerol at 90° C. and 50 m bar vacuum in the course of 1.5 hours. Afterwards, the product was neutralized using 2.6 g of acetic acid and bleached using 1.5 g of $H_2O_2$ (50% strength) at 90° C. in the course of 30 minutes. The reaction mixture was finally filtered at 90° C. and 0.5 bar pressure with addition of filter aid, CELITE®, 2 g, without solvent. A pale yellow viscous mass of composition B was obtained (see Table 1 which follows).

The composition was in each case determined by gas chromatography.

TABLE 1

| Product composition | Product A % by weight | Product B % by weight |
| --- | --- | --- |
| Glycerol | — | <0.5 |
| SE | 82.0 | 79.5 |
| Glycerides | — | 7.5 |
| FAME | 2.9 | <0.5 |
| FA | 8.5 | 7.5 |
| Sucrose | 5.0 | 3.3 |
| unidentified | 1.6 | 1.3 |
| SE | 82.0 | — |
| SGL | — | 87.0 |

SE: Sucrose ester
FAME: Fatty acid methyl ester
FA: Fatty acid
SGL: Sucrose glyceride

EXAMPLE 2

A mixture of 283.5 g (1.17 mol) of methyl myristate, 145.39 g (0.43 mol) of sucrose, 5 g of potassium carbonate and 5 g of zinc stearate was reacted as in Example 1 in the course of 5 hours. The reaction product A (see Table 2) was then treated with 17.5 g of glycerol at 90° C. and 50 mbar vacuum and filtered with addition of 2 g of kieselguhr filter aid (Seitz Ultra). A pale, cream-colored product of composition B (see Table 2) was obtained. The composition was in each case determined by gas chromatography.

TABLE 2

| Product composition | Product A % by weight | Product B % by weight |
| --- | --- | --- |
| Glycerol | — | <0.5 |
| SE | 81.0 | 67.0 |
| Glycerides | — | 17.5 |
| FAME | 3.7 | <0.5 |
| FA | 6.9 | 8.5 |
| Sucrose | 5.0 | 2.3 |
| unidentified | 3.4 | 3.5 |
| SE | 81.0 | — |
| SGL | — | 84.5 |

EXAMPLE 3

A mixture of 190.8 g (0.89 mol) of methyl laurate, 94.57 g (0.33 mol) of methyl palmitate/stearate, 4 g of potassium carbonate and 4 g of magnesium stearate was reacted as in Example 1 with 152.38 g (0.445 mol) of sucrose in the course of 5 hours. Product A was obtained (see Table 3). The product was treated with 10 g of glycerol at 90° C. and 50 mbar vacuum as in Example 1, bleached and filtered with addition of 2 g of filter aid. A pale product of composition B (see Table 3) was obtained. The composition was in each case determined by gas chromatography.

TABLE 3

| Product composition | Product A % by weight | Product B by weight |
| --- | --- | --- |
| Glycerol | — | <0.50 |
| SE | 81.50 | 74.50 |
| Glycerides | — | 6.50 |
| FAME | 2.69 | <0.5 |
| FA | 9.00 | 8.50 |
| Sucrose | 5.20 | 3.0 |
| unidentified | 1.61 | 6.50 |
| SE | 81.50 | — |
| SGL | — | 81.0 |

EXAMPLE 4

A mixture of 212 g (0.786 mol) of methyl palmitate, 57.37 g (0.27 mol) of methyl laurate, 5 g of potassium oxide, 5 g of sodium stearate and 122.5 g of sucrose (0.36 mol) was reacted as in Example 1. The reaction product (A) (see Table 4) was then reacted with 15 g of glycerol, bleached and filtered (B) (see Table 4).

The composition was in each case determined by gas chromatography.

TABLE 4

| Product composition | Product A % by weight | Product B % by weight |
| --- | --- | --- |
| Glycerol | — | <0.50 |
| SE | 80.00 | 74.00 |
| Glycerides | — | 12.50 |
| FAME | 8.15 | <0.5 |
| FA | 8.00 | 7.50 |
| Sucrose | 3.00 | 1.50 |
| unidentified | 0.84 | 3.50 |
| SE | 80.00 | — |
| SGL | — | 86.50 |

What is claimed is:

1. A process for the solvent-free preparation of sucrose fatty acid esters, comprising
   (a) reacting sucrose with one or more fatty acid alkyl esters selected from esters wherein the fatty acid radical is straight-chain or branched, saturated, mono- or polyunsaturated and contains 6 to 20 carbon atoms, in the presence of a basic catalyst at reduced pressure and elevated temperature, and then
   (b) reacting the reaction mixture formed in step (a) at reduced pressure and elevated temperature with 0.01 to 0.5 mol of polyol per mole of fatty acid alkyl ester employed in step (a), wherein the polyol reacts with unreacted fatty acid alkyl ester in the reaction mixture formed in step (a), and then
   (c) filtering the reaction product of step (b), wherein steps (a), (b), and (c) are carried out without addition of solvent.

2. The process as claimed in claim 1, wherein the polyol is glycerol.

3. The process as claimed in claim 1, wherein said one or more fatty acid alkyl esters are selected from esters having a chain length of 12 to 18 carbon atoms in the fatty acid radical.

4. The process as claimed in claim 1, wherein said one or more fatty acid alkyl esters are selected from esters having a chain length of 1 to 6 carbon atoms in the alcohol radical.

5. The process as claimed in claim 1, wherein one or more fatty acid methyl esters are employed in step (a).

6. The process as claimed in claim 1, wherein the amount of catalyst used is 0.5 to 5% by weight based on the total weight of the reaction mixture in step (a).

7. The process as claimed in claim 6, wherein the catalyst is selected from the group consisting of alkali metal hydroxides, alkali metal carbonates and metal soaps of straight-chain and branched, saturated, mono- or polyunsaturated fatty acids containing 6 to 20 carbon atoms.

8. The process as claimed in claim 6, wherein the catalyst is selected from the group consisting of sodium hydroxide, potassium hydroxide, potassium carbonate, cesium carbonate, and metal soaps of sodium, potassium, magnesium, zinc, tin and lithium with straight-chain and branched, saturated, mono- or polyunsaturated fatty acids containing 6 to 20 carbon atoms.

9. The process as claimed in claim 1, wherein the reaction according to process step (a) is carried out at temperature in the range from 120 to 160° C., and a pressure from 25 to 100 mbar in the course of 2 to 6 hours.

10. The process as claimed in claim 1, wherein the reaction in step a) is carried out using an at least equimolar ratio of fatty acid alkyl ester to sucrose.

11. The process as claimed in claim 1, wherein the reaction in step (a) is carried out using a molar ratio of fatty acid alkyl ester to sucrose in the range from 1:1 to 3.5:1.

12. The process as claimed in claim 1, wherein the reaction in process step (b) is carried out at a temperature from 90 to 130° C. and a pressure from 25 to 100 mbar for 0.5 to 3 hours.

13. The process as claimed in claim 1, wherein the filtration in process step (c) is carried out at 80 to 100° C. and at a pressure of 0.5 to 2 bar, optionally in the presence of 0.5 to 2% by weight of filter aid.

* * * * *